United States Patent [19]
Paris et al.

[11] 3,988,446
[45] Oct. 26, 1976

[54] GLYCERIDES WITH ANTI-INFLAMMATORY PROPERTIES
[75] Inventors: Gérard Yvon Paris, Duvernay; David Lyon Garmaise, Montreal, both of Canada
[73] Assignee: Abbott Laboratories, North Chicago, Ill.
[22] Filed: Nov. 7, 1974
[21] Appl. No.: 521,727

[52] U.S. Cl. .................. 424/230; 260/326.41; 260/326.13 A; 260/410.7; 260/410.8; 260/474; 260/473 F; 260/486 R; 260/488 J; 260/476 R; 424/274; 424/311
[51] Int. Cl.$^2$ ............... C07D 209/04; C07D 207/24; C11C 3/02; C07C 69/52
[58] Field of Search..... 260/410.7, 410.8, 326.13 A, 260/326.41, 326.46, 486 R, 488 J, 476 R, 474, 473 F; 424/230, 274, 307–309, 234, 313, 311

[56] References Cited
UNITED STATES PATENTS

| | | |
|---|---|---|
| 3,119,739 | 1/1964 | Campbell............................ 424/230 |
| 3,279,990 | 10/1966 | Rose .................................... 424/230 |
| 3,316,260 | 4/1967 | Shen ........................... 260/326.13 A |
| 3,468,907 | 9/1969 | Sherlock .................... 260/326.13 A |
| 3,579,535 | 5/1971 | Denss................................260/326.41 |
| 3,644,424 | 2/1972 | Sherlock ......................... 260/474 X |
| 3,652,609 | 3/1972 | Alburn............................. 260/410.7 |
| 3,673,212 | 6/1972 | Denss............................. 260/326.41 |
| 3,767,801 | 10/1973 | Tuma............................... 260/410.7 |

Primary Examiner—Winston A. Douglas
Assistant Examiner—John F. Niebling
Attorney, Agent, or Firm—Paul D. Burgauer; Robert L. Niblack

[57] ABSTRACT

Triglycerides carrying the anti-inflammatory drug moiety in the 2-position and hydrocarbon acyl moieties in the 1- and 3-position exhibit excellent anti-inflammatory properties without causing the side effects often associated with the anti-inflammatory drug itself.

11 Claims, No Drawings

GLYCERIDES WITH ANTI-INFLAMMATORY PROPERTIES

Anti-inflammatories are widely used for the treatment of inflammations associated with rheumatism and similar disease which are very often chronic in nature. In these instances, treatment with anti-inflammatory compositions is required to be continued for prolonged periods of time, often on a permanent or at least semi-permanent basis. Unfortunately, most of the anti-inflammatories used today are of the nature that causes discomforts, pains or even more severe disorders in the gastric tract. Experimentally, animals receiving only half the oral lethal dose, show moderate to severe stomach lesions on single dose administration of a standard anti-inflammatory drug and in humans, ulcers, gastric bleedings, and the like are frequently seen upon chronic administration of anti-inflammatory drugs.

It is therefore an object of the present invention to provide anti-inflammatory compositions that show improved tolerance by the gastric tract of warm-blooded animals. It is a further object of this invention to provide anti-inflammatory compositions for oral administration, which cause minimal or no stomach irritation. It is a particular object of this invention to provide new and better tolerated anti-inflammatories that are effective upon oral administration.

These and other objects are accomplished by providing a compound of the formula:

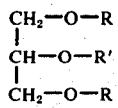

wherein R is an acyl derivative of the formula $CH_3$—X—CO— where X represents a saturated or unsaturated, divalent chain of 0 – 18 carbon atoms and wherein R' is the acyl moiety of an organic, pharmaceutically acceptable acid having anti-inflammatory properties.

The above acyl moiety having oral anti-inflammatory properties are the active principals of the most important anti-inflammatory compounds in use today as the most frequently described anti-inflammatories are organic acids. Specifically, R' includes the acyl derivatives of acetylsalicylic acid, α-(1-p-chlorobenzoyl-2-methyl-5-methoxy-3-indolyl)acetic acid, commonly referred to as indomethacin, 4-isobutylphenyl acetic acid, 2-(4-isobutylphenyl)-propionic acid, 4-allyloxy-3-chlorophenylacetic acid, 2-(6-methoxynaphthyl)-propionic acid, 1-methyl-5-(4-toluyl)pyrrole-2-acetic acid, 2-(4benzoylphenyl)propionic acid, 2-(3-phenoxyphenyl)-propionic acid, 5,8,11,14-eicosatetraynoic acid and the like.

Concerning substituent R, the acyl group contains a total of between two and 18 carbons and in the formula given above, X preferably represents the moiety —$(CH_2)_n$— wherein $n$ is 0 or an even integer; more specifically, acetyl, butyryl, hexanoyl, octanoyl, dodecanoyl, palmitoyl and the like.

In a general embodiment of the present invention, glycerol is diesterified first with the corresponding acid of formula $CH_3XCOOH$ to form the corresponding 1,3-dialkanoylglycerol (the term "alkanoyl" hereinafter is intended to represent $CH_3XCO$— with X having the above meaning) which in turn is esterified with the acid chloride of a known anti-inflammatory having a free carboxylic acid group. The preparation of such an acid chloride of an "anti-inflammatory acid" can ordinarily be made in known fashion by using phosphoros pentachloride, thionyl chloride, phosphorus oxychloride or other inorganic agents ordinarily used for such a conversion. These acid chlorides are usually quite stable and highly reactive so that the conversion required to make the above compound ordinarily succeeds in yields of 60 – 100% of theory.

In a more specific embodiment, dihydroxyacetone suspended in chloroform is cooled and after adding a minor proportion of pyridine, at least 2 molar equivalents of an alkanoyl chloride is added dropwise over a period of time. After stirring for several hours in an ice bath, the formed precipitate is removed and the 1,3-dialkanoyl dihydroxyacetone is worked up in known fashion. It is then taken up in a suitable solvent or solvent mixture and reduced, preferably using neutral sodium borohydride which produces the desired 1,3-dialkanoylglycerol which is isolated from the mixture in known fashion. This compound is then reacted, for instance, with about an equimolar amount of the acid chloride of indomethacin (hereinafter always referred to as indomethacoyl chloride) in the presence of a hydrochloric acid acceptor and a suitable organic solvent. Upon isolation and recrystallization, the formed triester of formula I is obtained in excellent purity.

Compounds made in this fashion can easily be compounded into dosage unit form for medicinal use. For instance, pharmaceutical tablets can be prepared by mixing this material with the usual type of adjuvants, flavoring agents, fillers, buffers and/or coloring agents which together with a lubricant can be compressed into the usual tablets. Also, a mixture of the above active compound with fillers and/or buffers or solid diluents can be processed into wafers, pills, or just simply filled into gelatin capsules in dosages of suitable amounts. Preferably, a dosage unit contains between 30 and 1000 mg. of the active ingredient, and if desired, other drugs can be admixed therewith.

Oral dosage forms of the type indicated above do not require any coating for the purpose of taste masking or protection against the acid environment of the stomach. The active ingredient is of very low acid and water solubility so that the taste requires no or little masking and stomach irritation is almost totally absent. Also, when the active ingredient reaches the intestinal tract, absorption takes place without irritating the gut. The active ingredient is lipid soluble and as such penetrates the cell membranes and will be found in the blood stream at sufficiently high doses to provide anti-inflammatory effect without irritating side effects for the intestinal or gastric tract.

As briefly mentioned above, the compounds of the present invention have unusually and surprising advantages over the compounds used by the prior art, namely the known anti-inflammatories which are incorporated into the esters of this invention. These advantages primarily comprise the almost total absence of lesions observed in experimental animals and, translated into other mammals, clearly indicates the substantial absence of any type of irritation in the gastro-intestinal tract. At the same time, the new compounds can be administered in the same or larger doses in order to produce a higher blood level of the anti-inflammatory component which enters the blood stream and/or lymphatic system as a triglyceride even though it is believed that for the brief moment of the molecule's passage through the membrane of the mucosa, the ester groups in the 1- and 3- positions are temporarily lost with prompt re-esterification within the mucosal cells and later in the blood or lymph system. This is of particular interest because anti-inflammatories usually have to be given on a permanent or semi-permanent basis which in the past has often led to serious damages of the gastro-intestinal tract of the consumer, causing irritation or intestinal bleedings as well as activating or reactivating ulcers. It is thus of particular interest to observe that with the triglyceride of the present invention, known anti-inflammatory moieties can be administered over extended periods of time without irritation; they are capable of producing prolonged or semi-permanent levels of the new active principal in the blood stream above the minimum effective level yet without ever surpassing, reaching or even approaching the toxic level.

In order to illustrate the method for preparing and using the new triglycerides, reference is made to the following examples which however, are not meant to limit the invention in any way.

EXAMPLE 1 a. Dihydroxyacetone dimer is dried for 4 hours in a vacuum pistol at 50° C.; 13 g. of the dry material is then suspended in 500 ml. of dry, ethanol-free chloroform in a 1-liter round-bottomed three-neck flask equipped with a calcium chloride drying tube and a pressure-equalizing dropping funnel. To this suspension at 5° C. is added 25 ml. of dry pyridine. The mixture is cooled in an ice bath while 76 g. of freshly distilled palmitoyl chloride is added dropwise over 1 hour. The reaction mixture is stirred at room temperature overnight. The precipitate of pyridine hydrochloride is filtered off and the chloroform solution is washed with 100 ml. portions of water. The chloroform solution is then evaporated to give a gummy solid which is triturated with a small amount of diethyl ether and filtered to give 52.2 g. of a white solid identified as 1,3-dipalmitoyldihydroxyacetone, melting at 79° – 82° C. and obtained in a yield of 64% of theory.

b. In a three-liter Erlenmeyer flask, 50.2 g. of the above compound is suspended in 1100 ml. of tetrahydrofuran and 250 ml. of benzene using mechanical stirring. The mixture is cooled to 5° C. and 70 ml. of water is added. The mixture is stirred and 5.02 g. of neutral sodium borohydride (made by stirring commercial sodium borohydride in ethyl acetate overnight, washing with ether and drying) in 0.5 g. quantities followed by stirring the suspension at 5° quantities for 45 minutes. At this time, 2.5 ml. of glacial acetic acid is added slowly to destroy excess borohydride and the mixture is stirred for 30 minutes at 5° C., before 300 ml. each of chloroform and diethyl ether are added. The mixture is washed with two 250 ml.-portions of water and subsequently with 250 ml. of a 1% sodium bicarbonate solution. The organic layer is then dried over anhydrous magnesium sulfate and evaporated to give a gummy solid. This material is triturated with a small amount of acetone and filtered to give 44.4 g. (88%) of 1,3-dipalmitoylglycerol as a while solid melting at 71° – 73° C.

c. To a stirred solution of 5.7 g. of the above diester and 0.95 g. of pyridine in 50 ml. of ethanol-free dry chloroform is added 3.76 g. of indomethacoyl chloride (prepared according to Spanish Pat. No. 341,692) under stirring. After standing for 40 hours, the reaction mixture is treated with 100 ml. of water. The chloroform layer is washed with 100 ml. of dilute hydrochloric acid, 100 ml. of 5% aqueous sodium bicarbonate and finally twice with 100 ml. of water, dried over sodium sulfate and evaporated. The solid residue obtained is dissolved in 100 ml. of petroleum ether boiling at 30° – 60° C. and chromatographed on a column containing 200 g. of Florisil (an activated magnesium silicate, marketed by Fisher Scientific Company, Ltd.) which was previously washed with petroleum ether. Some impurities are eluted first with petroleum ether and the column is then eluted with 85:15 petroluem ether/diethyl ether and finally with 50:50 petroleum ether/diethyl ether. The latter eluate contains the desired 2-indomethacoyl-1,3-dipalmitoylglycerol which is obtained in a yield of 6.2 g. (68%), melting at 64° – 66° C. Recrystallization from petroleum ether produces the pure material melting at 65° – 66° C. This compound has an intraperitoneal $LD_{50}$ of about 1000 mg./kg. and no oral toxicity.

EXAMPLE 2

The procedure of Example 1a is followed using 11.6 g. of 1,3-dihydroxyacetone and 58.2 g. of dodecanoyl chloride in 300 ml. of chloroform and 25 ml. of pyridine. The procedure yields 48.0 (82%) of 1,3-dodecanoyldihydroxyacetone melting at 67° – 70° C. which is triturated with methanol.

Upon treating this material according to the procedure shown in Example 1b, 1,3-didodecanoylglycerol is obtained in a yield 86% of theory as a white solid melting at 48° – 53° C.

By reacting 4.57 g. of this material with 4.14 g. of indomethacoyl chloride and 0.95 g. of pyridine in 50 ml. of chloroform for 60 hours as in example 1c, 2-indomethacoyl-1,3-didodecanoylglycerol is obtained in a yield of 4.3 g. (54%), melting at 51° – 52° C.

This compound also shows no oral toxicity and an intraperitoneal $LD_{50}$ of about 1000 mg./kg.

EXAMPLE 3

In analogy to Examples 1 and 2, 1,3-dihydroxyacetone is converted into the corresponding dioctanoyl ester which, upon crystallization from petroleum ether is obtained as a flaky solid melting at 57° – 58° C. in a yield of 70% of theory. Upon reducing this compound by the procedure of Example 1b, 1,3-dioctanoylglycerol is obtained as a clear oil in almost theoretical yield.

Upon reacting 5.65 g. of this oil with 6.17 g. of indomethacoyl chloride, 1.73 g. of pyridine in 200 ml. of dry chloroform for 20 hours as described in Example 1c, an oil is obtained which analyzes to the desired contents for 2-indomethacoyl-1,3-dioctanoylglycerol.

EXAMPLE 4

By following the procedure of Example 3, 1,3-dihydroxyacetone is converted to the corresponding 1,3-dibutyryl ester which is converted to the 1,3-dibutyrylglycerol. Upon treatment of this material with indomethacoyl chloride, 2-indomethacoyl-1,3-dibutyrylglycerol is obtained in a yield of 53% of theory as an oil.

EXAMPLE 5

By reacting 5.7 g. of the dipalmitoylglycerol of Example 1b with 2.18 g. of 2-acetylsalicyloyl chloride and 0.95 g. of pyridine in 50 ml. of chloroform for 4 days as described in Example 1c, 6.0 g. (82%) of 2-(2-acetylsalicyloyl)-1,3-dipalmitoylglycerol is obtained, melting at 43° – 44° C. This compound has an intraperitoneal $LD_{50}$ of about 1000 mg./kg. and no oral toxicity.

EXAMPLE 6

In analogy to Example 5, the 1,3-didodecanoylglycerol of Example 2 is converted to 2-(2-acetylsalicyloyl)-1,3-didodecanoylglycerol which is obtained in a yield of 61% of theory. It melts at 29° – 30° C.

EXAMPLE 7

In analogy with the preceding examples, 2-acetylsalicyloyl chloride is reacted with 1,3-dioctanoylglycerol which, upon work up as before, yields 71% of the desired 1,3-dioctanoyl-2-(2-acetylsalicyloyl)glycerol as an oil.

EXAMPLE 8

A solution of 5 g. of 4-allyloxy-3-chlorophenylacetic acid in 220.06 ml. of 0.1N sodium hydroxide is freeze-dried. The gummy solid is azeotroped three times with 200 ml. of dry benzene in vacuo to the sodium salt of the above acid. This is added, in portions to a solution of 5.08 g. of oxalyl chloride in 25 ml. of benzene. Another 25 ml. of benzene is added and the solution is gently refluxed for 1 hour, cooled, filtered and the filtrate is evaporated to yield 6 g. of a reddish yellow liquid identified as 4-allyloxy-3-chlorophenacetyl chloride.

Upon reaction of 5.7 g. of 1,3-dipalmitoylglycerol with 2.75 g. of 4-allyloxy-3-chlorophenacetyl chloride and 0.95 g. of pyridine in 50 ml. of chloroform for 18 hours as shown in Example 1c, 5.0 g. (64%) of 2-(4-allyloxy-3-chlorophenacetyl)-1,3-dipalmitoylglycerol, melting at 45° – 63° C., is obtained. This compounds shows no intraperitoneal or oral toxicity.

EXAMPLE 9

When in the process of Example 8 the 4-allyloxy-3-chlorophenacetyl chloride is replaced with 2.74 g. of 2-(6-methoxynaphthyl)-propionyl chloride (prepared from the free acid with oxalyl chloride as in Example 8) and the amount of solvent is increased to 70 ml., the reaction leads, in 60 hours, to a yield of 4.9 g. (63%) of 2-[2-(6-methoxynaphthyl)-propionyl]-1,3-dipalmitoylglycerol, melting at 66° – 68° C. This compound has no intraperitoneal and no oral toxicity.

EXAMPLE 10

A solution of 0.42 g. of oxalyl chloride in 25 ml. of chloroform is dropwise added at 0° to a stirred solution of 0.55 g. of eicosa-5,8,11,14-tetraynoic acid in 25 ml. of chloroform under nitrogen. Stirring is continued for 20 hours and the solvent is then removed under vacuum. The brownish residue is dissolved in 25 ml. of chloroform and the solution is added to 1.06 g. of 1,3-dipalmitoylglycerol and 0.15 g. of pyridine in 35 ml. of chloroform. After standing for 20 hours, the reaction mixture is chromatographed over 60 g. of Florisil as shown in Example 1, yielding 380 mg. (24%) of 2-(5,8,11,14-eicosatetraynoyl)-1,3-dipalmitoylglycerol. The product can easily be characterized by nmr spectroscopy but is unstable at room temperature when exposed to air.

EXAMPLE 11

In analogy to Example 4, the 1,3-diacetylglycerol is treated with indomethacoyl chloride in about equimolar amounts in dry chloroform yielding, after 16 hours, an oil at 66% of theory. Upon standing, this material crystallizes and shows a melting point of 78° – 80° C.

EXAMPLE 12

By following the procedure of Example 3, 1,3-dihydroxyacetone is esterified to the 1,3-dieicosanoyl ester which is obtained in a yield of 49% and melts at 89° – 90° C. after recrystallization from chloroform/petroleum ether. After reducing this ester according to Example 1b, 1,3-dieicosanoylglycerol is obtained in a yield of 85%; it melts at 83° – 84° C.

By reacting 3.41 g. of this diester with 7.07 g. of indomethacoyl chloride and 0.435 g. of pyridine in 75 ml. of dry chloroform for 60 hours according to Example 1c, 4.2 g. of 2-indomethacoyl-1,3-dieicosanoylglycerol is obtained; it melts at 70° – 72° C. after recrystallization from petroleum ether b.p. 30° – 60° C.

EXAMPLE 13

To a solution of 0.9 g. of dihydroxyacetone in 50 ml. of chloroform and 1.5 ml. of pyridine at 0° – 5° C. is added dropwise, 7.48 g. of freshly distilled linoleoyl chloride over a period of 15 minutes. The mixture is stirred for 1 day at room temperature, washed 3 times with 100 ml. of water and once with 100 ml. of brine. The organic phase is dried with magnesium sulfate and evaporated to leave 7.04 g. of a yellow oil. This is adsorbed on 40 g. of Florisil and extracted twice with 100 ml. of petroleum ether and twice with petroleum ether/ether 85:15. These last fractions are evaporated to give a clear, yellowish liquid (72% yield) characterized by infrared and nmr spectra as the 1,3-dilinoleoyl dihydroxyacetone.

This compound is hydrogenated according to Example 1b for 1.5 hours at 0° C., except that only chloroform is added before drying and evaporating which leaves a yellowish liquid (100% of yield) of 1,3-dilinoleoylglycerol, characterized by TLC and IR spectroscopy.

Reacting 3.7 g. of this compound with 2.26 g. of indomethacoyl chloride by the procedure of Example 1c yields 3.8 g. (67%) of 2-indomethacoyl-1,3-dilinoleoylglycerol characterized by nmr spectroscopy. This compound exhibits almost identical edema reduction properties as the compound of Example 1: at 21.6 mg./kg., edema reduces by 22.8%.

EXAMPLE 14

The compounds of the above examples were tested for their ability in reducing the swelling of artifically induced edema in rat paws caused by carageenan injection according to the procedure of Winter et al., Proc. Soc. Exp. Biol. Med., 111, 544 (1962). Table I gives the dose/effect data for the compound of Example 1 (containing 39.3% of the indomethacin moiety in the triglyceride molecule) and of the compound of Example 2 (44.8% indomethacin content). The control is carried out with indomethacin per se. In all instances, the amount shown is administered orally.

TABLE I

| Compound of Ex. | Time of Pre-Treatment | Dose in mg./kg. | % Edema Reduction |
| --- | --- | --- | --- |
| 1 | 30 – 60 Min. | 25 | 12 |
| 1 | 30 – 60 Min. | 50 | 18 |
| 1 | 2 hours | 25 | 29 |
| 1 | 2 hours | 50 | 26 |
| 1 | 4 hours | 50 | 38 |
| 1 | 8 hours | 50 | 20 |
| 2 | 2 hours | 11 | 36 |
| 2 | 2 hours | 25 | 51 |
| 2 | 2 hours | 50 | 43 |
| Control | 2 hours | 2.5 | 33 |
| Control | 2 hours | 5.0 | 44 |

The above results show that high levels of activity can be obtained with the new triglycerides. Particularly significant is the fact that the activity per indomethacin content of the administered compounds is very similar but causes no lesions in the case of the triglycerides. This is shown by sacrificing the animals that were given the above compounds at various doses: no lesions (0) were found in 6 animals receiving 16 mg./kg. of the compound of Example 1, no lesions in 6 animals at doses of 4 and 16 mg./kg. of the compound of Example 2; "free" indomethacin shows lesions in 3 animals of 6 at 4 mg./kg. and in 6 animals of 6 at 16 mg./kg. in rats.

In the same test, the compounds of Example 5 – 9 were compared with their respective controls. As "controls," the free acid of the acyl moiety attached to the 2-position of the new triglyceride was used. Table II shows this dose response.

TABLE II

| Compound of Ex. | Pre-treatment | Dose in Mg./kg. | % Edema Reduction | % of Control Moiety |
| --- | --- | --- | --- | --- |
| 5 | ½ hours | 200 | 3 | 24% |
| 6 | 2 hours | 200 | 11 | 29% |
| 7 | 2 hours | 200 | 15 | 35% |
| Control | 2 hours | 80 | 26 | free acid |
| 8 | 1 hour | 50 | 9 | 29% |
| 8 | 1 hour | 100 | 26 | 29% |
| 8 | 1 hour | 136 | 32 | 29% |
| Control | 2 hours | 20 | 38 | free acid |
| Control | 2 hours | 25 | 33 | free acid |
| 9 | 2 hours | 34 | 15 | 16% |
| Control | 2 hours | 2 | 41 | free acid |

In order to show the use of the above compounds for an extended time treatment, the method of Glen and Gray, Amer. J. Vet. Res., 26, 1180 (1965), was carried out with the new triglycerides. Upon orally administering 5 mg./kg. daily from day 14 to day 25 of the compound of Example 1, the hind paw rat edema shows on an increase of 0.62 ml. Hg. with the control vehicle showing 1.49 mg. Hg. On the visual score on all 4 limbs, the same treatment shows a score of 8.8 (16 is the theoretical maximum) with the control vehicle showing 13.6. Body weight gain is 63.3 g. in the treated animals and 45.4 g. in the control animals.

The compound of Example 2 given on days 14 – 25 shows the following results on day 25:

| Dose | Hind Paw Edema | Visual Score | Weight Gain |
| --- | --- | --- | --- |
| 2.2 mg./kg./day | 0.44 | 8.0 | 61.4 g. |
| 4.4 mg./kg./day | 0.55 | 6.4 | 69.3 g. |
| 8.8 mg./kg./day | 0.40 | 3.6 | 79.2 g. |

In no instance was there any observation of a gastric or intestinal irritation or bleeding.

In view of the extremely low toxicity of the above triglycerides of structure I and the extremely low incidents of lesions and gastric irritations, the new compounds are of great value in the treatment of inflammation and edema. They can be administered over extended periods of time without danger of gastric or intestinal bleedings, ulcers or the milder forms of irritations and upsets as is often the case with the free acids currently used as anti-inflammatories. The new compounds have extremely favorable therapeutic index values as in most instances, no toxicity could be established even with massive doses.

It will be obvious to those skilled in the art that the dosage of the new triglycerides to be administered to a large extent depends on the anti-inflammatory moiety in the triglyceride. Thus, for instance, where R' in the new triglyceride is the acetylsalicyloyl moiety, rather large doses are needed and are tolerated without discomfort. When R' is the indomethacoyl component, the total daily dose or single effective dose to be administered is much smaller. The dose also depends somewhat on the type of esters used for the 1- or 3-positions in the triglyceride. When R is a small moiety, i.e., X contains 0, 2, 4 or 6 carbon atoms, the proportion of R' in the triglyceride is considerably higher than when the compound is used wherein X contains 12 – 18 carbons. Thus, the selected dosage depends on the desired therapeutic activity of the moiety attached to the 2-position and the chain lengths of the aliphatic acid used for R.

In order to prepare capsules for oral administration, the following procedure is employed: 25 g. of the compound of Example 1 is preblended with 212.5 g. of lactose and 12.5 g. of talcum powder. The preblend is passed through a suitable screen and the screened powder is then blended and filled into gelatin capsules No. 3 to produce a filled weight of 250 mg. per capsule.

The following formulation is a typical tablet formula which may be used to incorporate the compounds of the present invention into tablet form. 13 g. of corn starch, 50 g. of the above triglyceride, 132 g. of calcium phosphate dibasic dihydrate, 1 g. of magnesium stearate and 4 g. of talcum powder with water q.s. to 200 g. Part of the above corn starch is milled together with the active drug and the calcium phosphate; this blend is milled and passed through a 40-mesh screen. The remaining portion of the corn starch is granulated with water, heated and mixed with the above blend in a hot air oven at 50° C. and sifted through a 16-mesh screen. The talcum powder and magnesium stearate are then added, the mixture is blended and subsequently passed through a 30-mesh screen and blended for at least 15 minutes. In order to prepare tablets, this mixture is compressed using a 9/32 inch standard convex punch producing a tablet of hardness 7 – 9 with each tablet weighing 200 mg. and containing 50 mg. of the active drug.

Of course, other pharmaceutically acceptable compositions can easily be prepared, e.g., suspensions, syrups, pills, wafers, and the like, preferably containing a predetermined amount of the active ingredient per given volume of such a dosage form. In case of liquid preparations for oral ingestion, a suitable nontoxic vehicle is used containing the necessary flavoring and sweetening agents to make up a liquid that is pleasant in taste and mouth feel.

What is claimed is:

1. A compound of the formula:

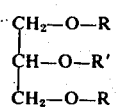

wherein R is an acyl derivative of the formula CH$_3$—X—CO— wherein X represents a saturated or unsaturated, divalent carbon chain of 0 – 18 carbon atoms and wherein R' is the acyl moiety of an pharmaceutically acceptable carboxylic acid, said acid having anti-inflammatory properties.

2. The compound of claim 1 wherein said acyl moiety R' is selected from the group consisting of acetylsalicyloyl, α-(1-p-chlorobenzoyl-2-methyl-5-methoxy-3-indolyl)acetyl, 4-allyloxy-3-chlorophenylacetyl, 2-(6-methoxy-naphthyl)-propionyl, 5,8,11,14-eicosatetraynoyl, 2-[3-chloro-4-(3-pyrrolinyl)phenyl]-propionyl, 2-(3-phenoxyphenyl)propionyl, 1-methyl-5-(4-tolyl)pyrrole-2-acetyl, 2-(4-benzoylphenyl)propionyl, 4-isobutylphenylacetyl and 4-isobutylphenylisopropionyl.

3. The compound of claim 1 wherein X is —(CH$_2$)$_{10}$— and R' is α-(1-p-chlorobenzoyl-2-methyl-5-methoxy-3-indolyl)acetyl.

4. The compound of claim 1 wherein X is —(CH$_2$)$_{10}$— and R' is 4-allyloxy-3-chlorophenylacetyl.

5. The compound of claim 1 wherein X is —(CH$_2$)$_{10}$— and R' is acetylsalicyloyl.

6. The compound of claim 1 wherein X is —(CH$_2$)$_{10}$— and R' is 4-isobutylphenylacetyl or 4-isobutylphenyl-2-propionyl.

7. The compound of claim 1 wherein X is —(CH$_2$)$_{10}$— and R' is 2-(6-methoxynaphthyl)propionyl.

8. A composition for alleviating the symptoms of inflammations consisting essentially of a compound of an anti-inflammatory effective amount of the formula:

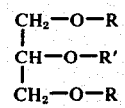

wherein R is an acyl derivative of the formula CH$_3$—X—CO— wherein X is a divalent saturated or unsaturated aliphatic chain of 0 – 18 carbon atoms and wherein R' is the acyl moiety of a pharmaceutically acceptable carboxylic acid having anti-inflammatory properties and a pharmaceutically acceptable carrier.

9. The composition of claim 8 in the form of a tablet for oral ingestion.

10. The composition of claim 9 wherein X is —(CH$_2$)$_{14}$— and R' is α-(1-p-chlorobenzoyl-2-methyl-5-methoxy-3-indolyl)acetyl.

11. The composition of claim 9 wherein X is —(CH$_2$)$_{14}$— and R' is acetylsalicyloyl.

* * * * *